(12) United States Patent
Jacquiod et al.

(10) Patent No.: US 8,349,445 B2
(45) Date of Patent: Jan. 8, 2013

(54) MICROBICIDAL SUBSTRATE

(75) Inventors: Catherine Jacquiod, Gif sur Yvette (FR); Léthicia Gueneau, Vincennes (FR); Sophie Vanpoulle, Gentilly (FR); Ronan Garrec, Asnieres sur Seine (FR); Jean-Gérard Leconte, Courbevoie (FR)

(73) Assignee: Saint-Gobain Glass France, Courbevoie (FR)

( * ) Notice: Subject to any disclaimer, the term of this patent is extended or adjusted under 35 U.S.C. 154(b) by 819 days.

(21) Appl. No.: 11/911,270

(22) PCT Filed: Apr. 10, 2006

(86) PCT No.: PCT/FR2006/050319
§ 371 (c)(1),
(2), (4) Date: Apr. 21, 2008

(87) PCT Pub. No.: WO2006/108985
PCT Pub. Date: Oct. 19, 2006

(65) Prior Publication Data
US 2009/0110918 A1    Apr. 30, 2009

(30) Foreign Application Priority Data

Apr. 11, 2005 (FR) ..................... 05 50921
Jul. 7, 2005 (FR) ..................... 05 52093

(51) Int. Cl.
*B32B 27/32* (2006.01)
*B32B 5/16* (2006.01)
*B32B 9/04* (2006.01)
*B32B 17/06* (2006.01)
*C23C 14/32* (2006.01)

(52) U.S. Cl. ........ 428/323; 428/220; 428/328; 428/332; 428/411.1; 428/426; 204/192.1; 204/192.11; 204/192.12

(58) Field of Classification Search .................... None
See application file for complete search history.

(56) References Cited

U.S. PATENT DOCUMENTS

| 6,037,289 | A | * | 3/2000 | Chopin et al. ................. 502/2 |
| 2002/0147108 | A1 | | 10/2002 | Sato et al. |
| 2004/0232819 | A1 | | 11/2004 | Huang et al. |
| 2006/0014050 | A1 | * | 1/2006 | Gueneau et al. ............. 428/702 |

FOREIGN PATENT DOCUMENTS

| EP | 0 870 530 | 10/1998 |
| EP | 1 205 243 | 5/2002 |
| JP | 2004-283769 | 10/2004 |
| WO | 03/087002 | 10/2003 |

* cited by examiner

*Primary Examiner* — Sheeba Ahmed
(74) *Attorney, Agent, or Firm* — Oblon, Spivak, McClelland, Maier & Neustadt, L.L.P.

(57) ABSTRACT

The invention relates to a substrate comprising at least one photocatalytic compound active under the conditions of illuminating an interior of a building or transport vehicle, intended to neutralize the microorganisms with which it comes into contact, and also to its preparation processes and its uses as glazing or another substrate for disinfection, filtration, ventilation, etc.

14 Claims, No Drawings

MICROBICIDAL SUBSTRATE

CROSS-REFERENCE TO RELATED APPLICATIONS

This application is a 371 of PCT/FR06/50319 filed Apr. 10, 2006 and claims the benefit of FR 0550921 filed Apr. 11, 2005 and FR 0552093 filed Jul. 7, 2005.

BACKGROUND OF THE INVENTION

Field of the Invention

The object of the present invention is to completely or partly destroy, or at least block the development of microorganisms such as bacteria, viruses and fungi, especially in a confined space such as the inside of a building or of a transport vehicle.

BRIEF SUMMARY OF THE INVENTION

The expression "blocking their development" is understood to mean that the amount of microorganisms is at the very most maintained, or slightly reduced: it is then referred to, for example, as a bacteriostatic functionality, whereas a bactericidal functionality denotes a more substantial reduction in the amount of bacteria.

Thus, the invention tackles, for example, the problems:
of all nosocomial infections of which the known sources may be the air, water, the hands or clothing of the occupants, the interior surfaces of the hospital; or else
of *legionellas* that form especially in water pipes, ventilation devices/ducts, air-conditioning systems, etc.

DETAILED DESCRIPTION OF THE INVENTION

The microorganisms targeted by the invention may or may not be pathogenic for humans. In particular, mention is made, non-limitingly, of:
as bacteria: *Bacillus, Bordetella, Borrelia, Brucella, Campylobacter, Chlamydophila, Clostridium, Corynebacterium diphteriae, Escherichia coli, Haemophilus influenzae, Legionella, Listeria, Mycobacterium leprae* and *tuberculosis, Mycoplasma, Neisseria, Pseudomonas, Salmonella, Staphylococcus, Streptococcus, Treponema pallidum, Vibrio cholerae, Yersinia pestis*, etc.
as viruses: SARS, AIDS, flu, hepatitis, herpes simplex, herpes zoster, *varicella*, corona virus, Ebola, etc.; and
as fungi: mycosis, *Aspergillus, Candida*, etc.

The object of the invention, defined above, is achieved by the invention, the subject of which is a substrate comprising at least one photocatalytic compound active under the conditions of illuminating an interior of a building or of a transport vehicle, intended to neutralize the microorganisms with which it comes into contact.

As a photocatalytic compound, one or more of the following compounds are understood: $TiO_2$, $WO_3$, $CdO_3$, $In_2O_3$, $Ag_2O$, $MnO_2$ and $Cu_2O_3$, $Fe_2O_3$, $V_2O_5$, $ZrO_2$, $RuO_2$ and $CR_2O_3$, $CoO_3$, NiO, $SnO_2$, $CeO_2$ and $Nb_2O_3$, $KTaO_3$ and $SrTiO_3$, $K_4NbO_{17}$, etc.

Most particularly preferred among these is $TiO_2$, at least partially crystallized in anatase and/or rutile form and, to a lesser extent, $SrTiO_3$ and $K_4NbO_{17}$.

The conditions for illuminating an interior of a building or of a transport vehicle are characterized by a spectrum composed mainly of visible light and of a small amount of residual ultraviolet light. The photocatalytic compound according to the invention is therefore chosen so as to be active under visible light, or to have a considerably augmented activity under ultraviolet light with respect to that of conventional photocatalytic compounds.

The term "to neutralize" is understood here to mean at the very least maintaining the starting amount of microorganisms; the invention excludes an increase of this amount. The development and proliferation of microorganisms are thus prevented and, in almost all cases, the surface area covered with microorganisms decreases, even in the case of maintaining their amount. The neutralization of the microorganisms may range according to the invention up to their complete destruction.

The neutralized microorganisms may be pathogenic for humans, in this case, the invention provides a benefit for human health. They may also be non-pathogenic for humans: it may then be a question of preserving the cleanliness of a transparent substrate by avoiding formation of fungi, etc.

According to a first variant, said photocatalytic compound comprises $TiO_2$ subjected to a heat treatment under an atmosphere of nitrogen or of nitrogen and of at least one reducing gas for a sufficient time to make it capable of absorbing photons from the visible spectrum. The heat treatment is carried out at a temperature of at least 250° C. and which may range up to 700° C., for a few fractions of seconds to a few hours. As a reducing gas, at least one from among hydrogen and hydrocarbons such as methane is used, the nitrogen/reducing gas(es) volume ratio being in particular between 100/0 and 50/50. The heat treatment is capable of corresponding to a conventional annealing treatment or to a conventional toughening treatment of a glass substrate.

According to a second variant, the substrate consists of a close combination of a first photocatalytic compound and a second compound having a bandgap between the upper level of its valence band and the lower level of its conduction band corresponding to a wavelength in the visible range. Said first photocatalytic compound is chosen from those already mentioned and said second compound from GaP, CdS, $KTa_{0.77}Nb_{0.23}O_3$, CdSe, $SrTiO_3$, $TiO_2$, ZnO, $Fe_2O_3$, $WO_3$, $Nb_2O_5$, $V_2O_5$, $Eu_2O_3$ in a non-limiting manner. The close combination of the two compounds may be obtained by a nonreactive process, for example, by mixing of powders and heat treatment in a binder, or by a liquid route after mixing of solutions, then heat treatment and/or drying. It may also be obtained by a reactive process such as a liquid or gas pyrolysis (thermal CVD) from precursors of the two compounds, or sputtering using a target composed, for example, of a mixture of two metal precursors of said first and second compounds.

The subject of both the first and second variant is the production of a compound that is photocatalytically active under illumination of the exclusively visible spectrum, the spectrum that is present as a majority in the inside of buildings or transport vehicles.

According to a third variant, said photocatalytic compound is integrated into a mesoporous structure. This structure based on at least one compound—especially an oxide—of at least one of the elements Si, W, Sb, Ti, Zr, Ta, V, B, Pb, Mg, Al, Mn, Co, Ni, Sn, Zn, In, Fe, Mo, etc. comprises a three-dimensional network of pores having diameters between 2 and 50 nm that communicate with one another. One embodiment of this variant consists of a mesoporous layer based on silica integrating nanoparticles of anatase crystallized $TiO_2$ having a size of around 50 nm. This layer may be obtained by a liquid route using structuring agents such as cetyltrimethylammonium bromide (CTAB) or polyoxyethylene/polyoxypropylene block copolymers which are degraded by heat treatment, leaving space for the mesopores. Reference is made to Application WO 03/87002 regarding the details of this process.

This third variant makes a substrate available of which the photocatalytic activity under ultraviolet radiation is considerably exacerbated, which is useful in the presence of a low illumination of residual ultraviolet light such as in the inside of a building, transport vehicle, etc.

According to this third variant, functional agents such as microbicides, deodorants, antibacterial agents or others are advantageously contained within the pores of the structure.

According to the three variants described previously, said photocatalytic compound advantageously comprises $TiO_2$ doped with N and/or S and/or at least one metal ion and, in particular:

$TiO_2$ doped with N is obtained by a liquid route from at least one precursor containing Ti in the presence of at least one compound having an ammonium functional group, then heat treatment; and $TiO_2$ doped with V, Cr, Mn, Mo, In, Sn, Fe, Ce, Co, Cu, Nd, Zn, W, Nb, Ta, Bi, Ni, Ru at a concentration of 0.5 to 10 mol % is obtained by coprecipitating a titanium compound such as an alkoxide and a metal salt, followed by a heat treatment.

Inserting at least one of these metal elements into the crystalline network of titanium oxide, the number of charge carriers was increased. This doping may thus be carried out only at the surface of the titanium oxide or where appropriate in the whole of the coating of which it is part, doping of the surface being carried out by covering at least part of the coating with a layer of metal salts or oxides.

Preferably, said photocatalytic compound, or at least part of the coating which incorporates it, are covered by a noble metal in the form of a thin film of Pt, Rh, Ag or Pd type. Thus, the photocatalytic phenomenon is amplified by increasing the yield and/or the kinetics of the photocatalytic reactions. Moreover, Ag is a microbicide.

Preferably, the substrate of the invention is based on glass or polymer(s), especially that are transparent, or a ceramic substrate, or glass-ceramic substrate or substrate made of architectural material of the type: facade render, concrete slabs or paving, architectonic concrete, concrete block, brick, tile, material of cementitious composition, terracotta, slate, stone, metallic surface, or a fibrous substrate based on glass of the mineral insulation wool type, or glass reinforcement yarn, fabric, material for coating walls of buildings such as wallpaper, or based on wood or paint.

In particular, the substrate of the invention is made of flat, especially soda-lime, glass. The term "flat" here denotes a substrate made of a monolithic or laminated plate that is plane or that has curved or bent sides, where appropriate assembled as multiple glazing delimiting at least one insulating gas-filled space.

In the case where the substrate is made of flat glass, said photocatalytic compound is advantageously combined with interposition of:

sublayers grown heteroepitaxially from said photocatalytic compound;

sublayers that form a barrier to the migration of alkali metals (especially of the soda-lime glass);

sublayers having an optical functionality;

sublayers having a thermal control; and/or sublayers that are conductive, antistatic, etc.

According to one particular advantageous embodiment, said compound is contained in a layer having a thickness between 5 nm and 1 µm.

As regards the process for depositing said photocatalytic compound, three main variants are recommended:

by room-temperature vacuum sputtering, where appropriate magnetron and/or ion-beam sputtering, using a metallic Ti or $TiO_x$ target with x<2 and an oxidizing atmosphere or using a $TiO_2$ target and an inert atmosphere;

by a solid, liquid or gas pyrolysis process of the CVD type; and by a sol-gel process.

Another subject of the invention is the use of the substrate described above:

as a surface for the inside of a public building such as a hospital or an individual house or apartment, or furniture, or of the inside of any terrestrial, water-borne or airborne transport vehicle, including clothing or any accessory worn by the occupant;

as self-cleaning, especially antifogging, antisoiling and anticondensation, glazing, especially for buildings of the multiple glazing type, double glazing, glazing for transport vehicles of the type: windshield, rear window or side window for an automobile, glazing for a train, plane or boat, utilitarian glazing such as glazing for an aquarium, shop window, greenhouse, interior furnishings—shelf or shower cubicle, for street furniture, mirrors, screens for display systems of the computer, television or telephone type, electrically operated glazing such as electrochromic, liquid crystal or electroluminescent glazing, photovoltaic glazing or glazing for a lamp; and in the filtration of liquids or gases, aeration and/or air-conditioning devices, ventilation ducts or water pipes.

The invention is illustrated by the following example.

EXAMPLE

Deposited onto the glass, still in the form of a ribbon of float glass was a sublayer based on silicon oxycarbide denoted for ease by SiOC (without prejudging the actual level of oxygen and of carbon in the coating)—the glass was a clear soda-lime-silica glass with a thickness of 4 mm, such as sold be Saint-Gobain Glass France under the name Planilux. This sublayer was deposited by CVD from Si precursors, in particular from a mixture of $SiH_4$ and ethylene diluted in nitrogen, using a nozzle positioned, above and transversely to the ribbon of float glass of a flat glass production line, within the float chamber, when the glass was still at a temperature of about 550 to 600° C. The coating obtained had a thickness of about 50 nm and a refractive index of about 1.55. Samples of 10 cm×10 cm in size were cut from the float glass provided with its SiOC alkali-metal barrier sublayer thus obtained; these samples were washed, rinsed, dried and subjected to a UV/ozone treatment for 45 minutes.

A coating with a mesoporous structure was formed on the sublayer.

The liquid treatment composition was obtained by mixing, in a first step 22.3 ml of tetraethoxysilane, 22.1 ml of absolute ethanol and 9 ml of HCl in demineralized water (pH 1.25) until the solution became clear, then by placing the round-bottomed flask in a water bath at 60° C. for 1 h.

In a second step, added to the sol obtained above was a solution of a polyoxyethylene/polyoxypropylene block copolymer sold by BASF under the registered trademark Pluronic PE6800 (molar weight 8000), in proportions such that the PE6800/Si molar ratio was 0.01. This was obtained by mixing 3.78 g of PE6800, 50 ml of ethanol and 25 ml of the sol.

The $TiO_2$ nanoparticles, crystallized as anatase and approximately 50 nm in size, were added to the liquid composition thus obtained just before deposition on the sample in an amount such that Ti/Si=1. The deposition was carried out by spin coating, with a starting amount of 3 ml per sample. (Other equivalent deposition techniques can be dip coating, spraying, laminar coating, roll coating, flow coating, etc.).

The samples were then subjected to the following annealing treatment:
30 min 100° C., 2 h hold;
15 min 150° C., 2 h hold;
15 min 175° C., 2 h hold;
10 min 200° C., no hold;
3 h 20 min 300° C., 1 h hold; and
2 h 30 min 450° C., 1 h hold.

The pores of the coating thus formed had a size of 4-5 nm.

By SIMS analysis of the coating with a mesoporous structure, it was confirmed that the Ti/Si atomic ratio was exactly identical to that of the initial liquid composition. SIMS analysis was also used to confirm that the nanoparticles were distributed uniformly in the three dimensions of the coating.

A comparative study was carried out of the adhesion, in dynamic conditions under ultraviolet radiation, of a bacterial culture on glass provided with the SiOC layer alone and on glass provided with the SiOC layer coated with the $TiO_2$ layer formed as described above.

A lamp characterized by a wavelength of 312 nm and a power of 100 W/m² was used.

The bacteria was *Staphylococcus epidermis* (ATCC 12228), distributed by American type culture collection. The strain kept in freeze-dried form was put back into suspension in 9 ml of TSB (trypto-case soy broth) and incubated for 15 hours at 37° C., then the cultures were divided up into cryotubes supplemented with glycerol (15%) and stored at −80° C. (main stock). TSB is a culture medium composition, of which 30 g of powder were diluted in one liter of distilled water (pH=7.3) and were distributed as follows:
bio-trypcase=17 g
bio-soyase=3 g
sodium chloride=5 g
potassium biphosphate=2.5 g
glucose=2.5 g In order to obtain the secondary stock or working stock, reculturing was carried out from the main stock in 200 ml of TSB. The broth was then incubated at 37° C. At the end of 24 h, 15% glycerol was added to protect the bacteria. The suspension obtained was then distributed into Eppendorf tubes (1 ml/tube) and kept at −20° C.

After rapid defrosting, the contents of an Eppendorf tube was removed and added to 9 ml of TSB (1st reculturing or R1). The broth was then incubated at 37° C. for 24 h. The second reculturing (R2) was carried out under similar conditions, except for the incubation time. Finally, 1 ml of R2 broth was removed and added to 200 ml of TSB (R3).

Monitoring of the growth made it possible to determine the beginning of the stationary phase achieved after incubating the R3 culture for 15 h. The study of bacterial adhesion will be carried out on the R3 culture aged for 17 hours, which corresponds to the stationary phase of bacterial growth.

The bacterial growth was evaluated by measurements of optical density (OD) as absorbance at the wavelength of 620 nm by using a Spectronic 401 spectrometer (Miltron Roy). 1 ml of the R3 suspension was removed at regular time intervals and added to a cuvette which was then placed in the spectrometer in order to measure the OD. The representation of the OD as a function of time constitutes the growth curve.

The medium used in the various experiments was physiological saline (solution of 0.15M NaCl or $\phi$ saline) or physiological saline diluted one hundred times (solution of 0.0015M NaCl or $\phi^{-2}$ saline). In order to have a bacterial suspension, the culture R3 was centrifuged three times for 10 minutes at 7000 rpm at a temperature of 4° C. The centrifugation pellet was resuspended either in $\phi$ saline, or in $\phi^{-2}$ saline depending on the techniques used (MATS, electrophoretic mobility, adhesion in static/dynamic conditions, etc.). The bacterial concentration was adjusted to a value of OD (as absorption). Thus, in order to ensure that the bacterial concentration is always of the same order of magnitude for a series of experiments, the suspension was diluted so as always to have the same OD value. In order to know the bacterial concentration, the method of counting the viable cells or counting on a solid medium is used.

The tests under dynamic conditions make it possible to monitor the kinetics of the process for bacterial adhesion on the solid surface. The support was placed in a dynamic adhesion cell. A bacterial suspension in $\phi$ saline of around $3\times10^6$ CFU/ml was circulated into the cell thanks to a peristaltic pump set at a flow rate of 15 ml/min in order to ensure a laminar regime (Re=10). The laminar regime, contrary to the turbulent regime, does not favor surface/microorganism impacts. Thus, the bacterial adhesion in this case does not depend on the flow conditions, but on the properties of the surfaces themselves and on the suspending liquid.

The adhesion of the microorganisms on the glass surface was monitored using a microscope (Leica, 10× magnification). A photo was taken every 10 minutes. By computer analysis of this photo, it was possible to determine the percentage of covering of each photo and thus build a curve which represents the percentage of covering of the surface by the bacteria as a function of the contact time.

The adhesion tests under dynamic conditions were carried out with the R3 culture aged for 22 hours.

It was observed that the degree of covering achieved constant values:
of 35% in 30 hours for bare glass;
of 15% in 20 hours for the $TiO_2$ glass.

Consequently, the bacteria adhere less well to the $TiO_2$ glass.

Moreover, in the examples of document WO 03/087002 using the same $TiO_2$ glass (mesoporous layer) glass, it was shown that this had a photocatalytic activity even under weak UW irradiation such as inside a building or a transport vehicle. It may be assumed that this photo-catalytic activity is not without effect on the bacteria themselves in order to explain their much lower level of covering.

Furthermore, still under the same weak UV irradiation, the $TiO_2$ glass becomes more hydrophilic. A flow of water may thus detach the bacterial cells, especially dead ones, from the surface of the $TiO_2$ glass more effectively than from the surface of the bare glass.

Thus, this example demonstrates the self-cleaning properties of the $TiO_2$ glass with respect to the bacteria tested.

This layer is therefore recommended for applications for destroying, at least partially, or stopping the development of microorganisms, especially indoors.

The invention claimed is:
1. A substrate comprising at least one photocatalytic compound active under the conditions of illuminating a building or transport vehicle interior, intended to neutralize the microorganisms with which it comes into contact,
(1) wherein said photocatalytic compound comprises $TiO_2$ subjected to a heat treatment under an atmosphere of nitrogen or of nitrogen and of at least one reducing gas for a sufficient time to make it capable of absorbing photons from the visible spectrum;

(2) wherein the substrate comprises a close combination of a first photocatalytic compound and a second compound having a bandgap between the upper level of its valence band and the lower level of its conduction band corresponding to a wavelength in the visible range; or (3) a combination of (1) and (2), wherein said photocatalytic compound comprises $TiO_2$ doped with N and/or S.

2. The substrate as claimed in claim 1, wherein said photocatalytic compound comprises $TiO_2$ subjected to a heat treatment under an atmosphere of nitrogen or of nitrogen and of at least one reducing gas for a sufficient time to make it capable of absorbing photons from the visible spectrum.

3. The substrate as claimed in claim 1, wherein $TiO_2$ doped with N is obtained by reacting, in a liquid, a mixture of at least one precursor containing Ti in the presence of at least one compound having an ammonium functional group, and then heat treating the mixture.

4. The substrate as claimed in claim 1, wherein said photocatalytic compound, or at least part of a coating which incorporates the photocatalytic compound is covered by a thin film comprising a noble metal which is Pt, Rh, Ag or Pd.

5. The substrate as claimed in claim 1, which is:
glass;
polymer(s);
a ceramic substrate;
glass-ceramic substrate;
facade render, a concrete slab, a concrete paver, architectonic concrete, concrete block, brick, tile, a material of cementitious composition, terracotta, slate, stone, a metallic surface, a fibrous substrate comprising glass mineral insulation wool, a glass reinforcement yarn, fabric, a material for coating a wall of a building;
wood; or
paint.

6. The substrate as claimed in claim 5, wherein the substrate comprises flat glass.

7. The substrate as claimed in claim 1, wherein said photocatalytic compound is contained in a layer having a thickness between 5 nm and 1 μm.

8. A process for preparing a substrate as claimed in claim 1, wherein said photocatalytic compound is deposited by room-temperature vacuum sputtering, using a metallic Ti or $TiO_x$ target with x<2 and an oxidizing atmosphere or using a $TiO_2$ target and an inert atmosphere.

9. The process for preparing a substrate as claimed in claim 8, wherein said photocatalytic compound is deposited by a solid CVD process, a liquid CVD process, or a gas pyrolysis CVD process.

10. The process for preparing a substrate as claimed in claim 8, wherein said photocatalytic compound is deposited by a sol-gel process.

11. The substrate as claimed in claim 6, wherein the substrate comprises soda-lime glass.

12. The process for preparing a substrate as claimed in claim 8, wherein the room-temperature vacuum sputtering is magnetron sputtering and/or ion-beam sputtering.

13. The substrate as claimed in claim 1, wherein the photocatalyic compound is capable of absorbing photons exclusively in the visible spectrum.

14. The substrate as claimed in claim 1, wherein the second compound is GaP, CdS, $KTa_{0.77}Nb_{0.23}O_3$, CdSe, $SrTiO_3$, $Nb_2O_5$, $V_2O_5$, or $Eu_2O_3$.

* * * * *